United States Patent [19]
Nicoletti

[11] Patent Number: 5,456,678
[45] Date of Patent: Oct. 10, 1995

[54] SAFETY DEVICE FOR TAKING SAMPLES AND PERFORMING INFUSIONS

[76] Inventor: Pio Nicoletti, Via Caseificio 2, 38049 Vigolo Vattaro, Italy

[21] Appl. No.: 218,193

[22] Filed: Mar. 28, 1994

[30] Foreign Application Priority Data

Mar. 29, 1993 [IT] Italy .................. VR93A0029

[51] Int. Cl.$^6$ .............. A61B 19/00; A61B 5/00; A61M 5/32
[52] U.S. Cl. .............. 604/413; 604/414; 128/764
[58] Field of Search ............ 604/195, 197, 604/198, 412, 413, 414; 128/760, 763, 764, 768, 770

[56] References Cited

U.S. PATENT DOCUMENTS

| | | | |
|---|---|---|---|
| 2,639,709 | 5/1953 | Volgenau | 128/764 |
| 3,190,547 | 6/1965 | Shanley | 604/413 |
| 3,826,260 | 7/1974 | Killinger | 604/413 |
| 3,872,867 | 3/1975 | Killinger | 604/413 |
| 4,059,112 | 11/1977 | Tischlinger | 604/413 |
| 4,169,475 | 10/1979 | Genese | 604/413 |
| 4,883,068 | 11/1989 | Dechow | 604/413 |

Primary Examiner—C. Fred Rosenbaum
Assistant Examiner—Frank Wilkens, III
Attorney, Agent, or Firm—Guido Modiano; Albert Josif

[57] ABSTRACT

Safety device for taking samples and performing infusions which comprises: a grip end provided with a coupling for connection to a fluid supply duct; a delivery end for a container for collecting fluid; a double-tip needle in which the tip proximal with respect to the supply duct is directed toward the grip end and the distal end is directed toward the delivery end; a needle support engaging an intermediate portion of the needle and movable from an inactive position to an active position toward the grip end in order to cause the proximal tip of the needle to penetrate the supply duct; elastic return means for said support; and an element for abutment at the delivery end for acting as a locator for a collection container, which moves with respect to the needle between a retracted needle protection position and a protruding position for insertion on the needle in order to expose its distal tip and simultaneously insert it in the collection container.

22 Claims, 5 Drawing Sheets

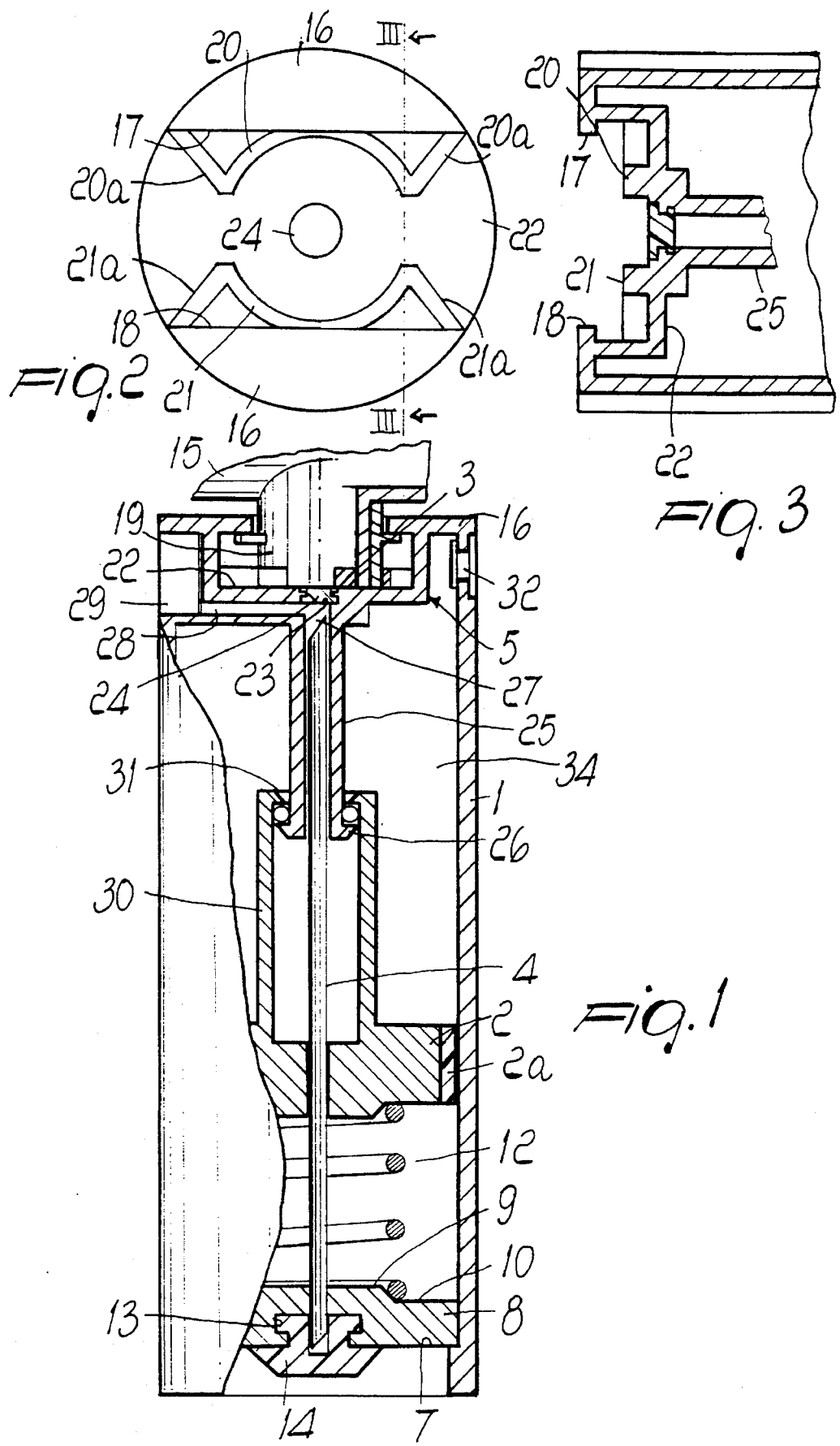

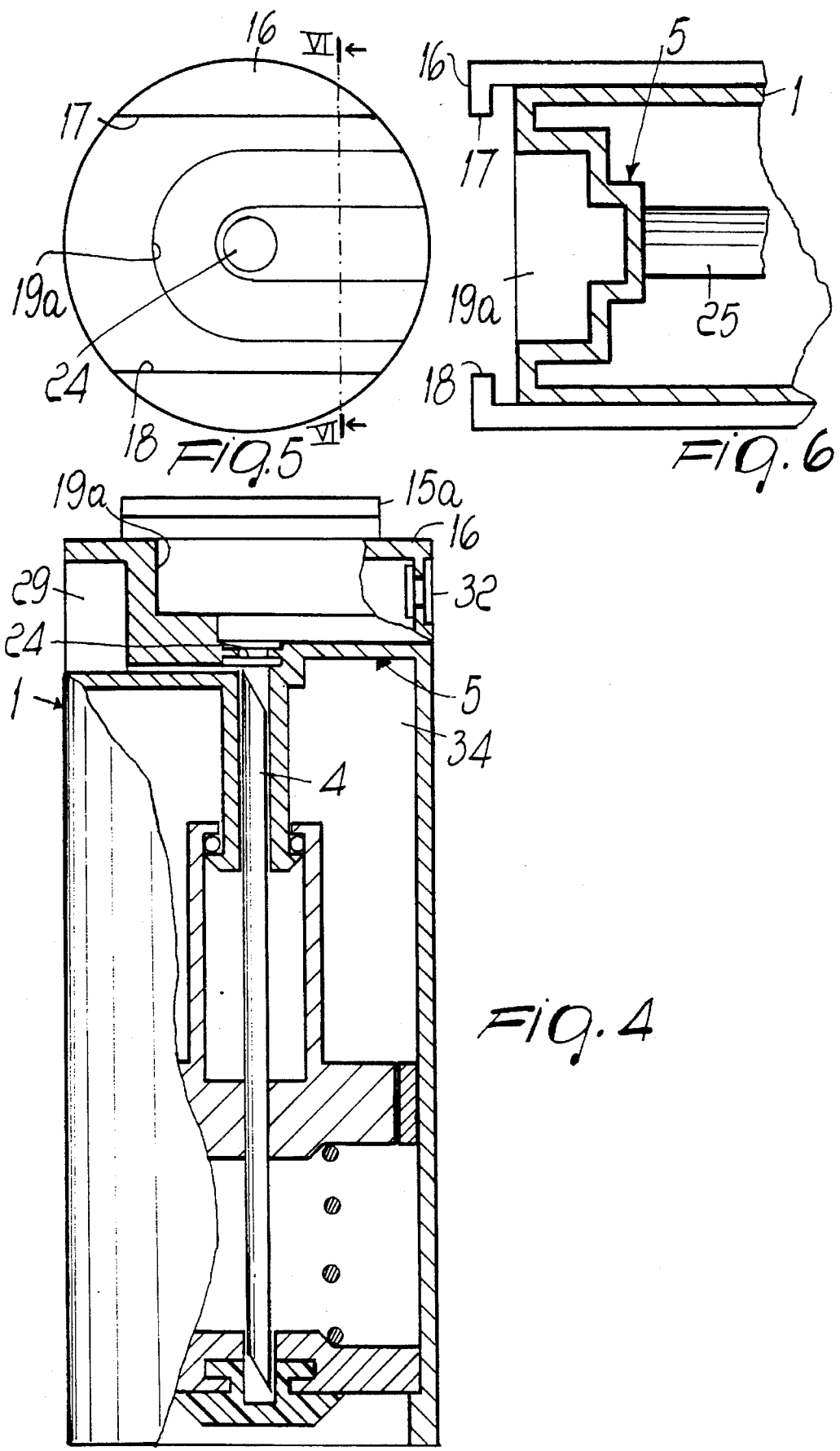

5,456,678

SAFETY DEVICE FOR TAKING SAMPLES AND PERFORMING INFUSIONS

BACKGROUND OF THE INVENTION

The present invention relates to a safety device for taking samples and performing infusions.

As is known, in assisting so-called "critical" patients and/or patients undergoing hemodialysis it is rather frequently necessary to take samples or carry out infusions for diagnostic and therapeutic purposes. During these procedures, the nursing personnel is exposed to severe risks of contact with biological liquids or dialysates that can be the source of infections, among which those transmitted by viruses, and typically hepatitis C and AIDS, are particularly relevant due to the severity and irreparable nature of the organic damage that they cause. AIDS, as is known, has a long incubation period, i.e. a long period during which risk patients can be contagious although no objective symptoms or specific laboratory data are detected to that effect.

The statistically most frequent method of contagion for nursing staff is injury caused by accidental percutaneous puncture.

SUMMARY OF THE INVENTION

The aim of the present invention is to provide a safety device that eliminates the danger of accidental puncture for health staff when taking samples or carrying out infusions of blood, drugs and liquids.

An object of the present invention is to provide a safety device that is safe and effective in operation, is easy to use and has a modest production cost.

With this aim, this object and others in view, which will become apparent hereinafter, there is provided, according to the present invention, a safety device for taking samples and performing infusions which comprises: a grip end provided with a coupling for connection to a fluid supply duct; a delivery end for a container for collecting or infusing fluid; a double-tip needle in which the tip that is proximal with respect to the supply duct is directed toward the grip end and the distal end is directed toward the delivery end; a needle support that engages an intermediate portion of the needle and can be moved from an inactive position to an active position toward the grip end in order to make the proximal tip of the needle penetrate into the supply duct; first elastic return means for said support; and an element for abutment at the delivery end which acts as a locator for a collection container and moves, with respect to the needle, between a retracted needle protection position and a protruding position for insertion on the needle in order to expose its distal tip and simultaneously insert it in the collection container, so that during use first the needle support is moved into its active position while the abutment element simultaneously moves into the protruding position for the penetration of the proximal tip of the needle into the supply duct and of its distal tip into the collection or infusion container. Subsequently the needle support is returned to the inactive position, with the consequent exit of the proximal tip from the supply duct and then, in sequence, the abutment element moves backward into the retracted position and the collection or infusion container is simultaneously moved away from the distal end of the needle.

Advantageously there are second elastic return means for the abutment element which are weaker than the first return means, so that by pressing a collection container against the abutment element one sequentially or simultaneously moves said abutment element toward the needle support, simultaneously causing the distal end of the needle to exit therefrom to enter the container, and moving the needle support into its active position in order to connect the supply duct to the container by means of the needle; whereas by releasing the pressure on the container said first return means return the needle support to its inactive position, and the abutment element is subsequently or simultaneously pushed, into its retracted position by the "static" retention elements.

The safety device according to the invention is used particularly in dialysis, where it can be applied to blood lines of an extracorporeal circuit or to the lines of a dialysis liquid, which have sample withdrawal points that are closed by a respective pierceable stopper; the device can also be used in intensive and sub-intensive therapies when patients are intubated with venous or arterial catheters.

The safety device according to the invention is used specifically in dialysis, where it can be applied to the blood delivery lines of an extracorporeal circuit or to the lines for the dialysis liquid, as well as to the venous or arterial catheters used to intubate patients subjected to intensive and sub-intensive therapies.

BRIEF DESCRIPTION OF THE DRAWINGS

Further aspects and advantages of the present invention will become apparent from the following detailed description of some examples of preferred embodiments thereof, given merely by way of non-limitative example with reference to the accompanying drawings, wherein:

FIG. 1 is a cutout view of a first embodiment of the safety device;

FIG. 2 is a top view, i.e. a view taken from the proximal end, of the safety device of FIG. 1;

FIG. 3 is a partial sectional view, taken along the plane III—III of FIG. 2;

FIGS. 4, 5 and 6 are similar to FIGS. 1 to 3, but relate to a different embodiment;

DESCRIPTION OF THE PREFERRED EMBODIMENTS

Figure 8:
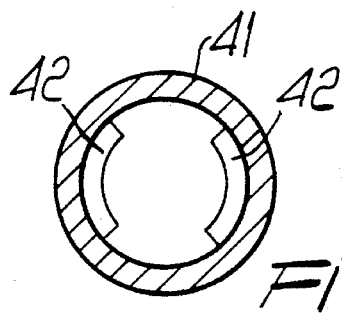
FIG. 8 is a sectional view, taken along the plane VIII—VIII of FIG. 7.
Figure 10:
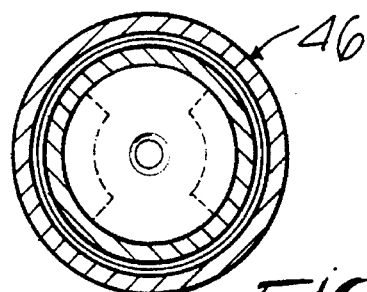
FIG. 10 is a sectional view, taken along the plane X—X of FIG. 9.

In the accompanying drawings, identical or similar parts or components have been designated by the same reference numerals.

As can be seen from the drawings, a safety device 6 according to the embodiments shown in FIGS. 1 to 3 and 4 to 6 is of the pressurization type and includes: a support, which comprises for example a unit with a cylinder 1 and a piston 2 (provided with a sliding and sealing gasket 2a) and supports a double-tip syringe needle 4; and a quick connector 5 for connection to a withdrawal or infusion duct or line 15 which is closed by a pierceable stopper 3. The cylinder or jacket 1 has two diameters so as to delimit at its distal end an inner shoulder 7 which can also be inclined or flared and against which it is possible to abut a supporting disk 8 which constitutes an abutment element, as explained further hereinafter. The disk 8 can have, at its inner face, a central raised portion 9 to delimit an annular peripheral region 10 which forms an abutment seat for an end of a return spring 12 the other end whereof reacts against the piston 2, whereas said disk forms, at its outer face, an accommodation and retention seat 13 for a pierceable stopper 14 made of rubber or of another suitable material.

The cylinder 1 can be made of a suitable plastic material, such as PVC, polyethylene, polypropylene, ABS, etc., both rigid and flexible under pressure, and can be formed with one or more parts or segments. On the outside of the distal end, if desired, it is possible to provide a removable protection stopper to maintain aseptic conditions and a grip for the fingers of the operator; both the stopper and the grip are not shown in the drawings.

At its proximal end, the cylinder or jacket 1 is closed at its top by a partition 16 being part of the quick-coupling connector 5 that is shaped like a female element for detachable connection to the line 15 for conveying blood or dialysis liquid or for supplying arterial or venous catheters or to a line for diagnostic investigations. More particularly, the connector 5 has a box-like shape and has two straight and parallel opposite inner edges 17 and 18 at the top partition 16 which are meant to act as a guide for sliding insertion on a union 19 that is part of the line 15. Insertion can occur by elastic flexing of the walls or by shape mating if the union is ovalized or of the snap-together, quick-coupling pitch, or Luer-Lock type. A pair of opposite ridges 20 and 21 is provided at a recessed level with respect to the guiding walls 17 and 18; said ridges rise from a wall 22 which is parallel to the partition 16 but is recessed with respect to it.

The ridges 20 and 21, like the edges 17 and 18, are arranged in a mirror-symmetrical manner with respect to the longitudinal axis of the device 6 and are configured so as to have at both of their ends two inclined portions, respectively 20a and 21a, that act as a guide, and an inner portion 20b and 21b which is shaped like a cradle for accommodating and retaining the union 19. The device 6 is thus locked by means of its wings against the partition 16.

The connector 5 is centrally provided, in its wall 22, at its face directed toward the partition 16, with a seat 23 for accommodating a pierceable membrane or stopper 24 and has, at its opposite face, a hollow axial flap 25 that is provided with a flanged end 26.

If desired, the inner passage section 27 of the protrusion 25 can be vented by means of a lateral duct 28 and an antibacterial filter 29 which is preferably accommodated between the connector 5 and the jacket 1.

The protrusion 25 is arranged to engage (for example enter) telescopically and abut against an axial protrusion 30, which is also hollow and provided with a flanged end 31, of the piston or displacement element 2, which as mentioned supports the axial double-tip needle 4 which is fixed to it and extends on one side through the protrusions 30 and 25 and, on its other side, through the disk 8, so that it can penetrate through one or the other of the stoppers or diaphragm 14 or 3 and 24. The maximum stroke of the piston 2 and therefore of the needle 32 is determined by the length of the protrusions 25 and 30; the first protrusion can abut against the connector 5 and the second protrusion can abut against the piston 2.

A check valve 32 is provided in an appropriate position between the connector 5 and the jacket 1 to pressurize the internal cavity 34 of the jacket 1.

The operation of the safety device 6 described above is extremely simple and safe. In inactive conditions, it assumes the configuration shown in FIG. 1, in which the union 19 of the line 15 is sealingly closed by the stoppers 3 and 24 made of rubber latex, in front of the proximal end of the needle 4. The other end of the needle 4 is in front of the stopper 14 and is preferably partially inserted into it; said stopper 14 is also made of rubber latex and advantageously has a frustum-like shape on the outside of the disk 8 to allow easy hermetic engagement against the edge of a sample withdrawal test tube (not shown). The stopper 14 can in fact act as a reflux-preventing element if the distal tip pierces the stopper 24 and the stopper 3 first and also as a static retention element in order to temporarily keep the cylinder and the needle joined during the removal of the needle.

In order to keep the disk 8 and the piston 2 temporarily joined during the first step of removal, it is possible to provide appropriate engagement elements which can be variously shaped, for example an elastic male-female coupling, which will also be described hereafter.

To perform a withdrawal it is sufficient to apply a test tube with a pierceable stopper against the static retention element 14 and push it against the disk 8 so as to move said disk in contrast with the action of the spring 12, which in turn moves the piston 2 in contrast with the resistance of the air compressed within the cavity 34 and moves, together with said piston, the needle 4, which is forced to simultaneously pierce both the withdrawal stoppers 24 and 3 and the reflux-preventing retention element 14 as well as the stopper of the test tube. During these movements, the needle 4 remains perfectly axially aligned since it is guided both by the protrusion 25 and by the disk 8. The liquid, for example blood, can then flow from the line 15 to the needle 4 and then to the test tube.

Once the preset dose of liquid has been collected, the operator removes pressure from the test tube, moving it away from the device 6. The elastic compressive force of the air in the internal opening 34 simultaneously moves the needle 4 backward, moving it away from the union 19 until it exits from the stoppers 3 and 24. By virtue of the pressure differential applied to the piston by the spring 12 on one side and by the compressed air on the other side, the tip of the needle 4 that lies proximate to the line 15 exits from the stoppers 3 and 24; in other words, it leaves the withdrawal point before the other tip of the needle exits from the test tube, so that the residual liquid still present in the needle is also aspirated into the test tube. The needle is vented for this purpose along the duct 28 with the interposition of the antibacterial filter 29 to avoid contaminations. Finally, the spring 12 returns the disk 8 against the shoulder 7, thus returning the safety device into its inactive or initial position, ready for a new withdrawal of a sample.

In the embodiment illustrated in FIGS. 4 to 6, the safety device can be applied to a line 15 by insertion on a pair of finger protection wings 15a and by abutment of the union 19 against a shoulder 19a provided in the connector 5.

Figure 7:
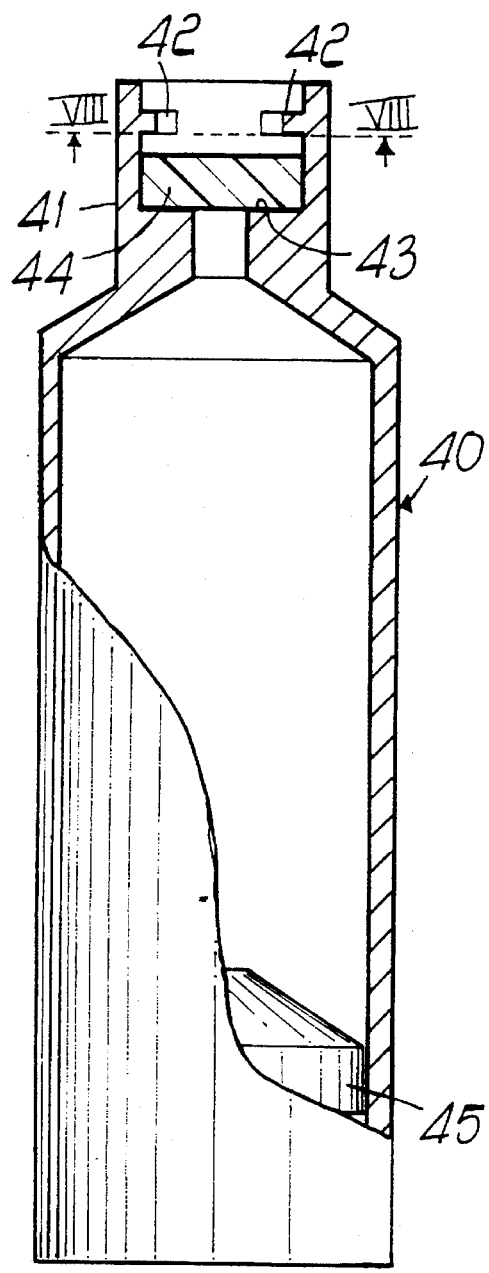
FIG. 7 is a partially sectional elevation view of a withdrawal or infusion vial that can be used as a syringe with the safety device according to the invention.
Figure 9:
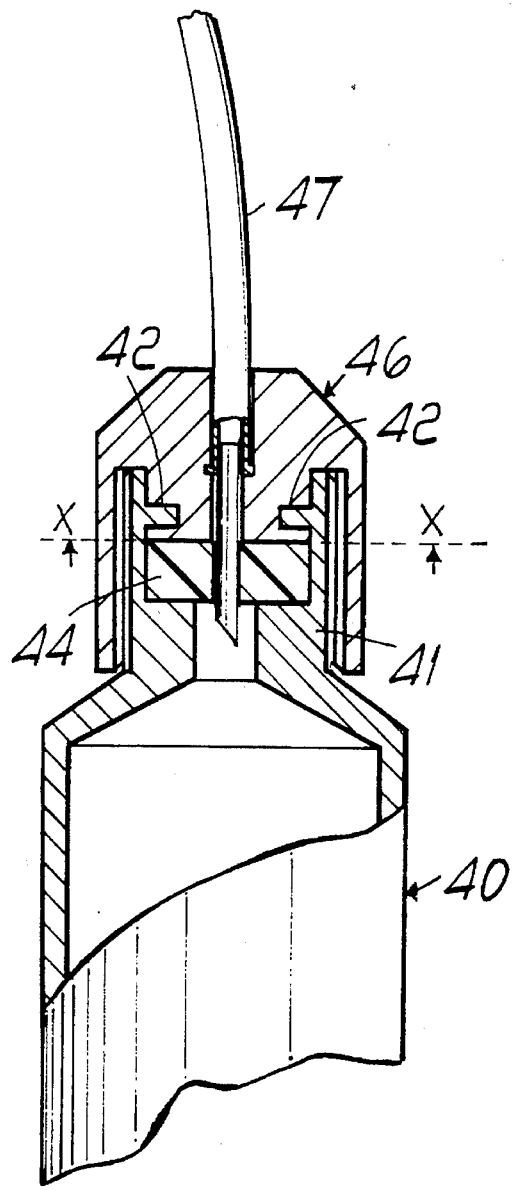
FIG. 9 illustrates the tip of the vial of FIG. 8, provided with an insert that has a needle to fill it by aspiration or to discharge sterile substances.

FIGS. 7 to 9 illustrate a vial that can be used both for sample withdrawals and infusions with a safety device 6 described above and as a syringe. For this purpose, the vial 40 has a neck 41 having two diametrically opposite inner wings 42 beyond which there is an inner abutment shoulder 43 for a rubber latex closing stopper 44. A plunger 45 is slidingly mounted in the body of the vial and can be actuated by means of a stem that is operated from the outside of the body of the vial, as is usual in syringes.

Figure 11:
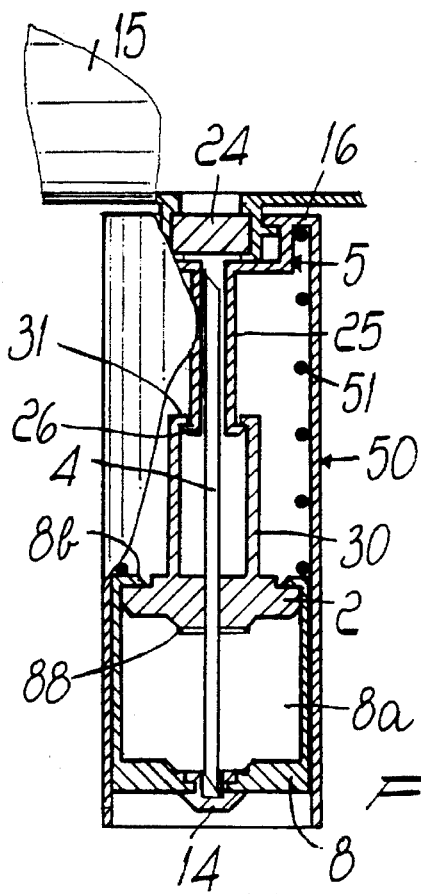
FIG. 11 is a partially sectional view of another embodiment of the safety device according to the invention.
Figure 12:
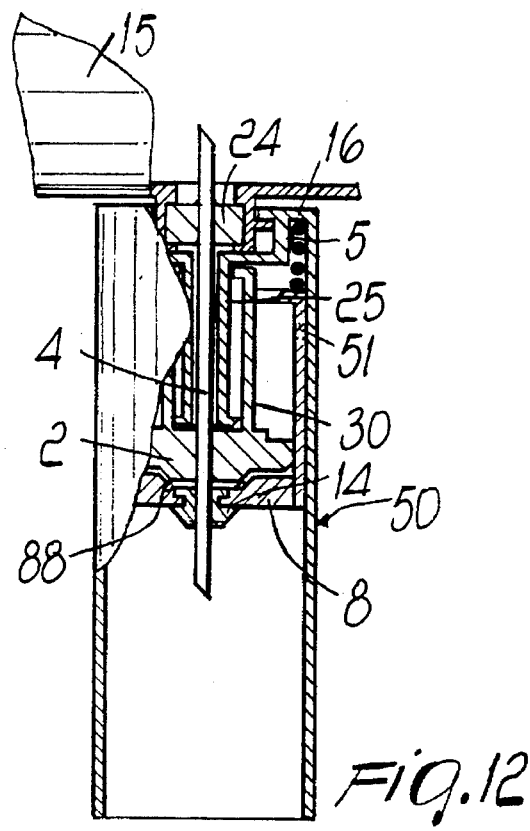
FIG. 12 is a partially sectional view of the safety device of FIG. 11 in a different operating position.

Once the rim of the neck 41 of the vial 40 has been moved so that it abuts against the stopper 14 of the device 6 of FIG. 1 or of the device 50 of FIGS. 11 and 12, it is possible to push the vial fully against it to withdraw liquid into the vial or perform an infusion (i.e with a flow directed from the vial toward the line 15) of liquid in the above described manner. A needle-holder cap 46 is applied to the vial, and its needle 47 can be rigid, with a double tip, in order to aspirate sterile liquids, or can be flexible, as illustrated in FIG. 9, in which case it can be used to discharge the biological liquid drawn from a patient or from a line. During application, the cap firmly and detachably anchors to the wings 42, whereas the needle 47 pierces the stopper 44 and passes therethrough, ready to receive liquid from the inside of the vial when the plunger 45 is actuated.

The safety device 50 illustrated in FIGS. 11 and 12 is a currently preferred embodiment of the present invention, and its disk 8 constitutes the end plate of a telescopic tube 8a that has an internal end flange 8b and inside which the piston 2 is slidingly mounted. A helical compression spring 51 acts between the flange 8b of the disk and the top partition 16 of the jacket 1.

Operation is clearly understandable from FIGS. 11 and 12. FIG. 11 in fact illustrates the safety device in its standby or inactive position, whereas FIG. 12 is a view of the same device in the active position for the withdrawal of liquid from the line 15; in this position, one of the tips of the needle 4, after passing through the stopper 24, draws from the line 15, and the other tip, after piercing the stopper 14, enters a vial (not shown) that can be a vial 40, so as to connect the line 15 to the vial. In this active position, the displacement element 2 abuts against the connector 5, whereas the end plate 8 abuts against the displacement element and remains temporarily coupled to it by virtue of the presence of snap-action engagement means which are constituted by a first temporary engagement means, for example constituted by an annular ridge 82 formed on the piston-like element, that can engage with second temporary engagement means on the abutment element, for example constituted by a recess 88.

During removal, first of all the needle 4 exits from the line 15, by virtue of the thrust of the spring 51 which acts first on the end plate 8 which in turn moves the displacement element 2. When the spring 51 has pushed the end plate 8 and the displacement element 2, which is rigidly coupled to the end plate 8, so that the locators 31 thereof abut against the flanged end 26, the end plate is made to separate from the displacement element to expel the test tube or vial from the needle. Then, as the return motion of the end plate 8 toward its inactive position continues, the other tip of the needle 4 leaves the vial to retract beyond the stopper 14; this therefore occurs after the needle has been able to discharge into the vial any residual liquid contained inside it.

Figure 13:
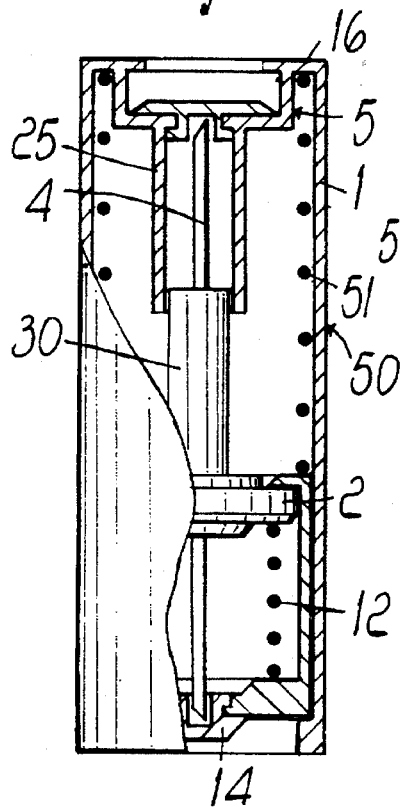
FIGS. 13, 14 and 15 are sectional views of an equal number of embodiments of the device according to the invention.

FIG. 13 is a view of an embodiment which is similar to that of FIGS. 11 and 12 but has a piston 2 which is provided with a protrusion 30 that is telescopically inserted in the protrusion 25 of the connector 5 which acts as a sliding guide.

Figure 14:
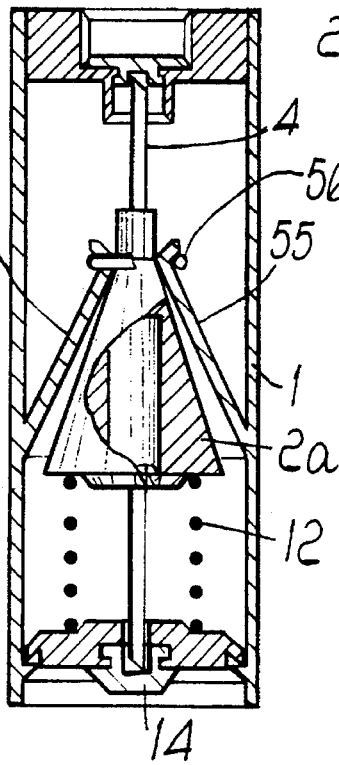

The embodiment illustrated in FIG. 14 is a variation of the safety device, in which instead of the piston 2 there is a frustum-like element 2a acting as an inclined plane for abutment with lateral protrusions 55 that protrude in a cantilevered manner from the inside of the jacket 1 and are preferably held together in an elastically flexible manner and concentrically to the needle 4 by an elastic ring 56 to return the cone into its inactive position.

Figure 15:
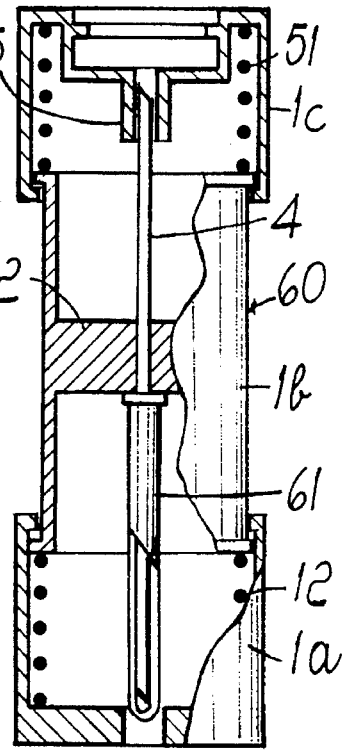

FIG. 15 is a view of a safety device 60 with a jacket 1 comprising three telescopic elements 1a, 1b and 1c. The intermediate element 1b is rigidly coupled to the needle 32 and supports it, and the end of said needle which is directed toward the distal element 1a is sheathed within a pierceable sheath 61. Advantageously, the elements 1a and 1c may also be of the bellows-like type.

Figure 16:
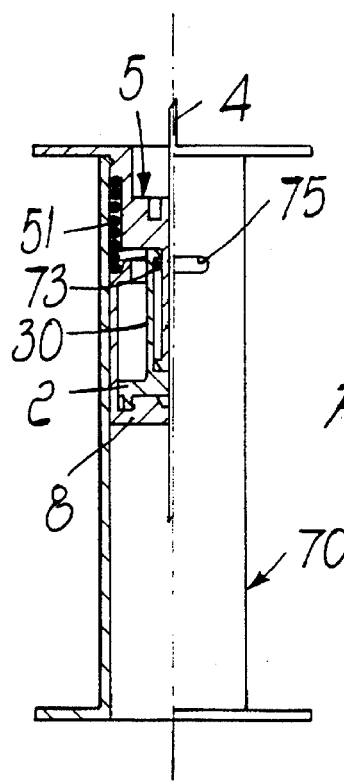
FIGS. 16 and 17 are partially sectional views of a variation of the embodiment of FIGS. 11 and 12, shown in two different operating positions.
Figure 18:
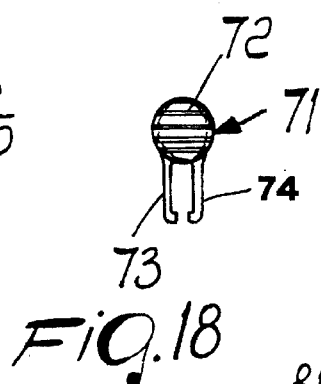
FIG. 18 shows a detachable retention element.
Figure 17:
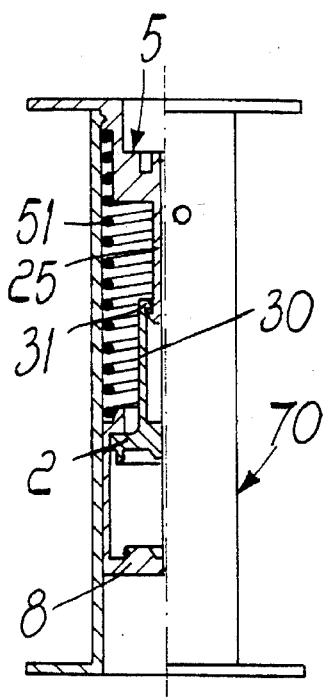

The safety device 70 shown in FIGS. 16, 17 and 18 is similar to the one shown in FIGS. 11 and 12, but the needle support can be locked, for example by means of a removable clip 71, in the operating position for drawing liquid from a feed line. The clip 71 can be configured in any suitable manner and can have, for example (FIG. 18), a tab 72 which remains on the outside and in view on the cylinder 70 and two arms 73 and 74 which are insertable in an appropriate seat 75 in the cylinder 70 to fit, for example, below the flanged end 31 in order to retain the axial protrusion 30 and thus the displacement element 2 pressed in contrast with the force of the spring 51.

The safety device 70, used in combination with a vial 40 of FIGS. 7 to 10, can be used as a catheter which, at the end of a withdrawal of a sample, for example of blood, allows to retract the needle 4 automatically and by actuation, i.e. by removing the clip 71, without using means for capping said needle. The spring 51 subsequently ensures that the needle 4 remains in a retracted and accordingly protected position.

The safety device 70 furthermore allows to use multiple vials 40 in succession, while the needle remains in its operating position, for example inserted in a vein.

Figure 19:
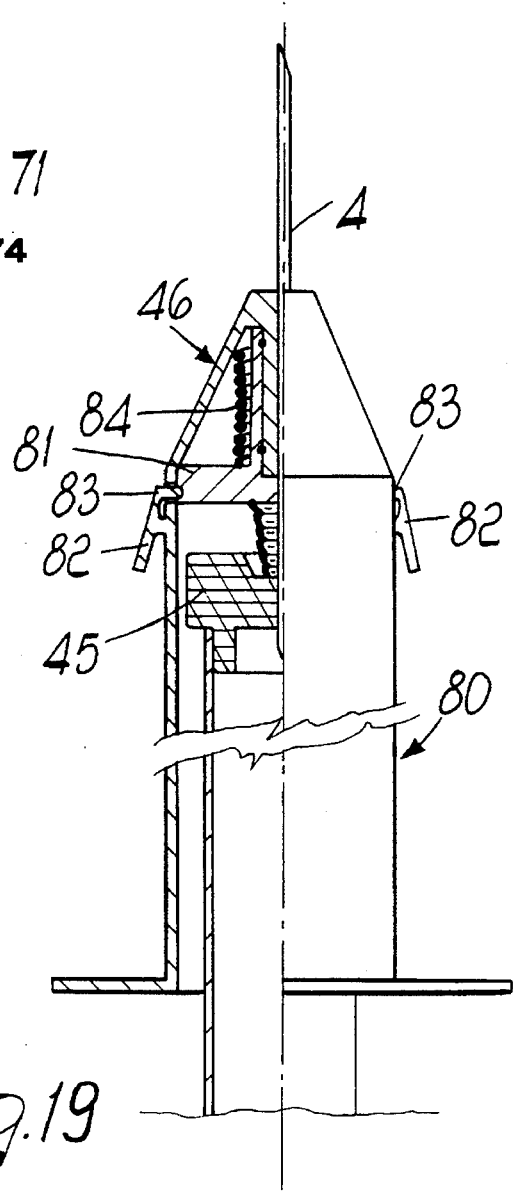
FIGS. 19 and 20 are partially sectional views, in different scales, of a further embodiment of the safety device according to the invention.
Figure 20:
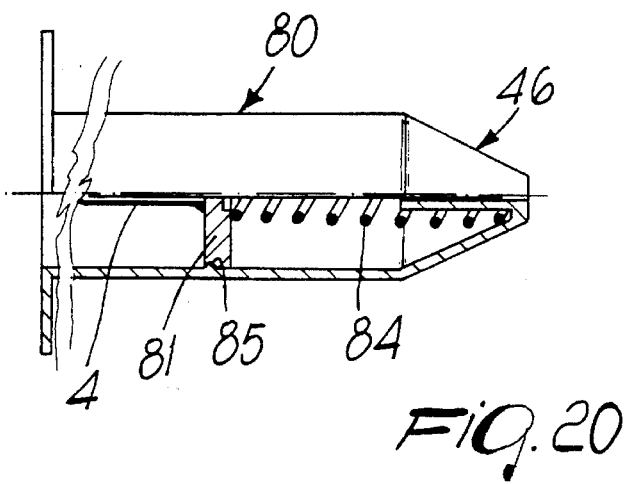

FIGS. 19 and 20 illustrate a vial-syringe 80 which is a different embodiment of the vial 40 and in which the needle 4 can move through the cap 46 and is rigidly supported by a supporting disk 81. On the outside of the body 80 of the vial there is a pair of diametrically opposite clips 82 that are shaped for example like a lever and are meant to enter, with a slanted end 83, the distal end of the vial to engage the disk 81 and retain it in position. Said disk is loaded by a spring 84, so that by pressing the two clips 82 with one's fingers, for example when a blood withdrawal is complete, the disk is pushed toward the inside of the vial 80, thus automatically retracting the needle 4 (FIG. 20) into a protected position, where the disk 81 can optionally engage a ridge 85 in a snap-together manner.

The above described safety device is susceptible to numerous modifications and variations within the scope of the protection defined by the content of the following claims.

Thus, for example, the connection between the withdrawal point and the safety device can provide for coupling by screwing, for example with a quick-coupling pitch, with snap-together means or the like.

The materials and the dimensions may be various according to the requirements.

I claim:

1. Safety device for taking samples and performing infusions comprising a cylinder;

a piston-like element slidingly guided within said cylinder;

said cylinder and said piston-like element forming a needle support;

said needle support having a proximal end suitable to be connected to a fluid supply duct and a delivery end;

a double tip needle axially slidingly supported by said needle support;

a quick coupling connector comprising guiding protrusions provided with flanges, said connector being provided at said proximal end to connect said safety device to said fluid supply duct;

an abutment element provided at said delivery end;

first elastic return means interposed between said piston-like element and an element which during the sliding of said piston-like element is independent of said sliding;

a first pierceable stopper closing said quick coupling connector;

a second pierceable stopper closing said abutment element and suitable to connect said safety device to a container; said double tip needle being moved from an inactive position to an active position in which the tips thereof concurrently penetrate through said first and second stoppers to provide communication between said fluid supply duct and said container.

2. Safety device according to claim 1, wherein said first elastic return means are interposed between said proximal end and said abutment element.

3. Safety device according to claim 1, wherein said flanges of said guiding protrusions form a mutual engagement with said piston-like element.

4. Safety device according to claim 1, comprising first temporary engagement means on said piston-like element, and second temporary engagement means on said abutment element which, when engaged between each other, define a temporary engagement between said abutment element and said needle support.

5. Safety device according to claim 4, wherein said temporary engagement means comprise a detachable clip.

6. Safety device according to claim 4, wherein said temporary engagement means comprise at least one element to detachable engage said needle support, said engagement being externally releaseable.

7. Safety device according to claim 1, wherein said first elastic return means are interposed between said abutment element and said piston-like element.

8. Safety device according to claim 1, comprising second elastic return means interposed between said abutment element and said piston-like element.

9. Safety device according to claim 8, wherein said second elastic return means are weaker than said first elastic return means so that, by pressing a collection container against said abutment element, said abutment element is moved sequentially or simultaneously toward the piston-like element, so that simultaneously the tip of the needle directed toward the abutment element exits from said support to enter the container and the piston-like element moves into its active position to connect the supply duct to the container across the needle, whereas by releasing the pressure on said container said first elastic return means return the piston-like element into its inactive position and said abutment element is subsequently pushed into its retracted position.

10. Safety device according to claim 9, comprising a proximal coupling-supporting cylinder and a distal cylinder to support said abutment element so as to provide a telescopic engagement with said piston-like element.

11. Safety device according to claim 1, wherein said needle support element comprises a surface shaped like an inclined plane that slidingly engages expanding elastic return means.

12. Safety device for taking samples and performing infusions comprising a needle support having a proximal end suitable to be connected to a fluid supply duct and a delivery end;

a double tip needle axially slidingly supported by said needle support;

a quick coupling connector comprising guiding protrusions provided with flanges, said connector being provided at said proximal end to connect said safety device to said fluid supply duct;

an abutment element provided at said delivery end;

first elastic return means interposed between said proximal end and said abutment element;

a first pierceable stopper closing said quick coupling connector;

a second pierceable stopper closing said abutment element and suitable to connect said safety device to a container;

first temporary engagement means on said piston-like element, and second temporary engagement means on said abutment element which, when engaged between each other, define a temporary engagement between said abutment element and said needle support;

said double tip needle being moved from an inactive position to an active position in which the tips thereof concurrently penetrate through said first and second stoppers to provide communication between said fluid supply duct and said container.

13. Safety device according to claim 12, wherein said needle support comprises a cylinder and a piston-like element slidingly guided within said cylinder.

14. Safety device according to claim 12, wherein said flanges of said guiding protrusions form a mutual engagement with said piston-like element.

15. Safety device according to claim 12, wherein said temporary engagement means comprise a detachable clip.

16. Safety device according to claim 12, wherein said temporary engagement means comprise at least one element to detachable engage said needle support, said engagement being externally releaseable.

17. Safety device according to claim 12, wherein said first elastic return means are interposed between said abutment element and said piston-like element.

18. Safety device according to claim 12, comprising second elastic return means interposed between said abutment element and said piston-like element.

19. Safety device according to claim 12, wherein said second elastic return means are weaker than said first elastic return means so that, by pressing a collection container against said abutment element, said abutment element is moved sequentially or simultaneously toward the piston-like element, so that simultaneously the tip of the needle directed toward the abutment element exits from said support to enter the container and the piston-like element moves into its active position to connect the supply duct to the container across the needle, whereas by releasing the pressure on said container said first elastic return means return the piston-like element into its inactive position and said abutment element is subsequently pushed into its retracted position.

20. Safety device according to claim 19, comprising a proximal coupling-supporting cylinder and a distal cylinder to support said abutment element so as to provide a telescopic engagement with said piston-like element.

21. Safety device according to claim 12, wherein said needle support element comprises a surface shaped like an inclined plane that slidingly engages expanding elastic return means.

22. Safety device for taking samples and performing infusions comprising an external jacket having a proximal end suitable to be connected to a fluid supply duct and a delivery end;

a telescopic tube having an end plate which closes said delivery end;

flanges provided on said telescopic tube in a position opposite to said delivery end;

a piston slidingly arranged within said telescopic tube;

a double tip needle axially slidingly supported within said piston;

a quick coupling connector provided at said proximal end to connect said safety device to a fluid supply duct, said quick coupling connector comprising guiding protrusions and flanges, said flanges being arranged for mutual engagement with said piston-like element at the inactive position thereof;

first elastic return means interposed between said proximal end and said abutment element;

a first pierceable stopper closing said quick coupling connector;

a second pierceable stopper closing said abutment element and suitable to connect said safety device to a container;

first temporary engagement means on said piston-like element, and second temporary engagement means on said abutment element which, when engaged between each other, define a temporary engagement between said abutment element and said piston-like element, said first temporary engagement means comprising an annular ridge formed at the bottom of said piston and said second temporary means comprising a recess formed in said end plate;

said double tip needle being moved from an inactive position to an active position in which the tips thereof concurrently penetrate through said first and second stoppers to provide communication between said fluid supply duct and said container.

\* \* \* \* \*